United States Patent [19]

Stein

[11] 3,975,412

[45] Aug. 17, 1976

[54] MONO-ACYLATION OF 17-HYDROXY-3-ALKOXYGONA-2,5-(10)DIENES

[75] Inventor: Reinhardt P. Stein, Audubon, Pa.

[73] Assignee: American Home Products Corporation, New York, N.Y.

[22] Filed: Oct. 15, 1974

[21] Appl. No.: 514,675

[52] U.S. Cl............................ 260/397.4; 260/397.5
[51] Int. Cl.² ............................................ C07J 1/00
[58] Field of Search ................................. 260/397.4

[56] References Cited
UNITED STATES PATENTS 3,549,672  12/1970  Windholz et al................ 270/397.5

OTHER PUBLICATIONS

Liston et al., "J. Org. Chem." (1968) vol. 33 No. 8 pp. 3109–3113 relied on.

Primary Examiner—Elbert L. Roberts
Attorney, Agent, or Firm—Robert Wiser

[57] ABSTRACT

An efficient, one-step process for preparing 13-alkyl-17α alkyl, alkenyl, or alkynyl-17β-acyloxy-4-en-3-one steroids from their corresponding 13-alkyl-17α-substituted-3-alkoxygona-2,5(10)-dien-17β-ols is disclosed. Products of the instant process possess, for example, progestational activity.

5 Claims, No Drawings

MONO-ACYLATION OF 17-HYDROXY-3-ALKOXYGONA-2,5-(10)DIENES

BACKGROUND OF THE INVENTION

This invention relates to a process for preparing 13-alkyl-17α-substituted-17β-acyloxy-4-en-3-one steroids, wherein the 17α-substituent may be an alkyl, alkenyl, or alkynyl group. The 17β-hydroxy-precursors of these esters are well-known and in a totally synthetic process are prepared by hydrolysis of suitably substituted 3-alkoxy-2,5(10)-gonadienes (see for example U.K. Pat. Nos. 1,041,279 and 1,111,449). The 13-alkyl-17α-substituted-17β-acyloxy-4-en-3-one steroids are well-known for their pharmaceutical efficacy; thus, for example, norethindrone acetate is currently being marketed as an orally active progestational agent. A process for their synthesis which requires several steps is described in U.K. Pat. No. 1,113,813.

In this particular process 13β-ethyl-17α-ethynylgon-4-en-17β-ol-3-one is contacted with an acylating agent such as acetic anhydride producing 3,17β-diacetoxy-13β-ethyl-17α-ethynyl-3,5-diene. This diacylated material must next be selectively deacylated at the 3-position to produce the desired 17β-acetoxy-13β-ethyl-17α-ethynylgon-4-en-3-one. It can be seen that in this process the conditions necessary for the acylation of the 17β-hydroxy group of the 17β-hydroxygon-4-en-3-one are also sufficient to form the 3-enol acylate, which ester must be subsequently hydrolyzed by a carefully controlled preferential deacylation at the 3-position in order to produce the desired 17β-acetoxygon-4-en-3-one (see for example U.S. Pat. No. 2,964,537 and U.K. Pat. No. 1,113,813). It is also known that the acylation reaction itself must be carefully controlled in

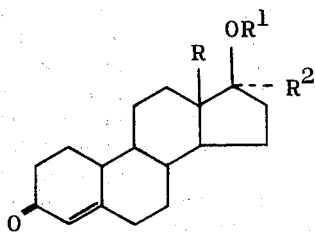

wherein R is alkyl of from 1 to 6 carbon atoms; $R^1$ is carboxylic acyl of from 1 to 4 carbon atoms; and $R^2$ is alkyl of from 1 to 6 carbon atoms, alkenyl of from 2 to 6 carbon atoms, or alkynyl of from 2 to 6 carbon atoms; which comprises treating a compound of the structure:

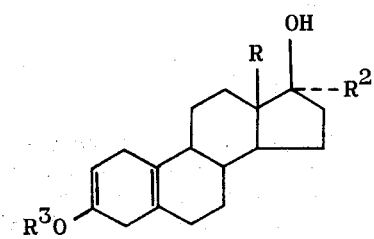

wherein R and $R^2$ are as defined above and $R^3$ is alkyl of from 1 to 6 carbon atoms or cycloalkyl of from 3 to 7 carbon atoms; with perchloric acid and a compound of the formula $(R^1)_2O$ wherein $R^1$ is as defined above, utilizing an ester of formula $R^1OR^4$ as solvent wherein $R^1$ is as defined above and $R^4$ is alkyl of from 1 to 6 carbon atoms, for from about 1 to about 10 minutes.

DESCRIPTION OF THE INVENTION and brine solutions, dried over anhydrous sodium or magnesium sulfate, filtered and evaporated. The residue may next be treated with a base such as pyridine in a solvent such as methanol to decompose any residual anhydride, which treatment may be followed by evaporation of the solvents and recrystallization of the residue. Those skilled in the art will recognize that variations in the above-described methods, or various other methods, such as chromatography, may be used to separate and purify the product of the instant process, and the proper choice of these methods and variations is within the skill of the art.

It has been observed that the instant process works particularly well and efficiently when the amounts of the various reagents and reactants utilized are in the following proportions:

1. steroid substrate (1.0 g.)
2. lower alkanoic anhydride (9.6 ml.)
3. perchloric acid (0.02 ml.)
4. ester (100 ml.)

However, the choice of quantities of reactants and reagents utilized in the instant process is not a critical aspect of the invention, and the variation of these quantities for example to optimize a particular yield is within the skill of the art.

While the process may be utilized to prepare a variety of lower alkanoic acid esters, it has been found to work particularly well for the preparation of acetates. This particular aspect of the invention would thus require, in addition to the steroid substrate, the use of acetic anhydride, perchloric acid, and any of the various lower alkyl acetates as solvent, for example ethyl acetate.

The reaction has been observed to proceed very rapidly and efficient yields are obtained when reaction times of from 1 to 3 minutes are utilized. Reaction times of longer than 10 minutes should be avoided as these longer times would increase the likelihood of competing side reactions with concomitant reduction in yield of the desired product. Because of the short reaction times involved it may be advantageous, when performing a large scale reaction, to predissolve the steroid reactant in the ester of choice and add this solution to the anhydride/perchloric acid solution dissolved in the same ester. In small scale reactions, addition of the steroid substrate to the anhydride/perchloric acid solution in either solution or in solid form has been found to produce efficient results.

The following non-limiting examples further illustrate the best mode contemplated by the inventor for carrying out the process of the invention.

EXAMPLE 1 dl-13-Ethyl-17α-ethynyl-17-hydroxygon-4-en-3-one, acetate

Prepare a fresh solution of acetic anhydride (9.6 ml.) and 70% aqueous perchloric acid (0.02 ml.) in ethyl acetate (100 ml.) then add dl-13-ethyl-17α-ethynyl-3-methoxygona-2,5(10)-dien-17-ol (1.00 g.) as a solid, [Note, on larger scale reactions it may be advantageous to dissolve the substrate in ethyl acetate first to complete the reaction rapidly ] swirl for 1.5 minutes (clear) then quench the reaction by adding saturated aqueous sodium bicarbonate solution. Wash the ethyl acetate layer with saturated bicarbonate, brine and dry over anhydrous sodium sulfate. Filter, evaporate in vacuo then add methanol with a trace of pyridine and let stand for 2 hours. Evaporate in vacuo, pump dry then treat the residue in ether with decolorizing charcoal. Filter, evaporate and crystallize the residue from methanol to obtain 326 mg. of dl-13-ethyl-17α-ethynyl-17-hydroxygon-4-en-3-one, acetate; m.p. 163°–165°; $\lambda_{max}^{KBr}$ 3.10, 4.77, 5.68, 6.03 and 6.20 μ; $\lambda_{max}^{EtOH}$ 239 mμ (ε 16,700).

EXAMPLE 2 d-13-Ethyl-17α-ethynyl-17-hydroxygon-4-en-3-one, acetate

Prepare a fresh solution of acetic anhydride (9.6 ml.) and 70% aqueous perchloric acid (0.02 ml.) in ethyl acetate (100 ml.) then add d-13-ethyl-17α-ethynyl-3-methoxygona-2,5(10)-dien-17-ol (1.00 g.) as a solid or as a solution in ethyl acetate then swirl for 1 minute (clear). Quench by adding 1.5 ml. of water then saturated aqueous sodium bicarbonate solution. Wash the ethyl acetate layer with saturated bicarbonate, brine and dry over anhydrous sodium sulfate. Filter, evaporate in vacuo and cover the residue with methanol (40 ml.) and pyridine (0.2 ml.). Warm briefly on the steam-bath, cool and evaporate the solvent in vacuo. Pump dry then pass the residue in benzene through a short column of Florex, treat the eluate with decolorizing charcoal, filter and evaporate the solvent in vacuo. Crystallize the residue from isopropanol and recrystallize the solid obtained again from the same solvent to obtain 400 mg. of d-13-ethyl-17α-ethynyl-17-hydroxygon-4-en-3-one, acetate, m.p. 200°–202°C.; $\lambda_{max}^{KBr}$ 3.10, 4.76, 5.68, 6.02 and 6.19 μ. $[\alpha]_D^{26}$ - 26.58° (c, 1% in chloroform).

EXAMPLE 3 dl-13-Methyl-17α-ethynyl-17-hydroxygon-4-en-3-one, acetate

Prepare a fresh solution of acetic anhydride (4.8 ml.) and 70% aqueous perchloric acid (0.01 ml.) in ethyl acetate (50 ml.) then add dl-13-methyl-17α-ethynyl-3-methoxygona-2,5(10)-dien-17-Ol (0.5 g.) as a solid, swirl for 1.5 minutes then quench the reaction by adding saturated aqueous sodium bicarbonate solution. Wash the ethyl acetate layer with saturated bicarbonate, brine and dry over anhydrous sodium sulfate. Filter, evaporate in vacuo then add methanol with a trace of pyridine and let stand for 2 hours. Evaporate in vacuo, pump dry then treat the residue in ether with decolorizing charcoal. Filter, evaporate and crystallize the residue from methanol to obtain dl-13-methyl-17α-ethynyl-17-hydroxygon-4-en-3-one, acetate.

The subject matter which the applicant regards as his invention is particularly pointed out and distinctly claimed as follows:

1. A process for preparing a compound of the structure:

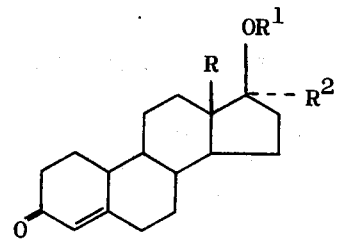

wherein R is alkyl of from 1 to 6 carbon atoms, $R^1$ is carboxylic acyl of from 1 to 4 carbon atoms, and $R^2$ is alkyl of from 1 to 6 carbon atoms, alkenyl of from 2 to 6 carbon atoms, or alkynyl of from 2 to 6 carbon atoms; which comprises treating a compound of the structure:

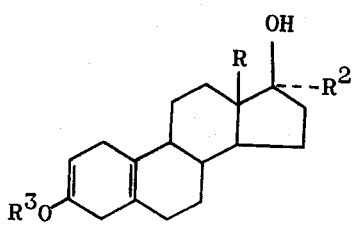

wherein R and $R^2$ are as defined above and $R^3$ is alkyl of from 1 to 6 carbon atoms or cycloalkyl of from 3 to 7 carbon atoms; with perchloric acid and a compound of the formula $(R^1)_2O$ wherein $R^1$ is as defined above, utilizing an ester of formula $R^1OR^4$ as solvent wherein $R^1$ is as defined above and $R^4$ is alkyl of from 1 to 6 carbon atoms for from about 1 to about 10 minutes.

2. The process of claim 1 wherein R is methyl.

3. The process of claim 1 wherein R is ethyl.

4. The process of claim 1 wherein R and $R^3$ are methyl, $R^1$ is ethanoyl, and $R^2$ is ethynyl.

5. The process of claim 1 wherein R is ethyl, $R^1$ is ethanoyl, $R^2$ is ethynyl, and $R^3$ is methyl.

* * * * *